(12) United States Patent
Radaelli et al.

(10) Patent No.: US 8,865,452 B2
(45) Date of Patent: Oct. 21, 2014

(54) SYSTEMS AND METHODS FOR EXTRACTING LIPIDS FROM WET ALGAL BIOMASS

(75) Inventors: Guido Radaelli, Oakland, CA (US); Daniel Fleischer, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 943 days.

(21) Appl. No.: 12/485,027

(22) Filed: Jun. 15, 2009

(65) Prior Publication Data

US 2010/0317088 A1 Dec. 16, 2010

(51) Int. Cl.
*C12N 1/06* (2006.01)
*C11B 1/10* (2006.01)
*C12P 7/64* (2006.01)

(52) U.S. Cl.
CPC ............... *C12P 7/6463* (2013.01); *C12N 1/066* (2013.01)
USPC .................................. 435/259; 554/20; 554/8

(58) Field of Classification Search
None
See application file for complete search history.

(56) References Cited

U.S. PATENT DOCUMENTS

| | | |
|---|---|---|
| 1,926,780 A | 9/1933 | Lippincott |
| 2,730,190 A | 1/1956 | Brown |
| 2,766,203 A | 10/1956 | Brown |
| 3,175,687 A | 3/1965 | Jones |
| 3,468,057 A | 9/1969 | Buisson |
| 3,897,000 A | 7/1975 | Mandt |
| 3,962,466 A * | 6/1976 | Nakabayashi ................. 426/60 |
| 4,003,337 A | 1/1977 | Moore |
| 4,159,944 A | 7/1979 | Erickson et al. |
| 4,253,271 A | 3/1981 | Raymond |
| 4,267,038 A | 5/1981 | Thompson |
| 4,341,038 A | 7/1982 | Bloch et al. |
| 4,365,938 A | 12/1982 | Warinner |
| 4,535,060 A | 8/1985 | Comai |
| 4,658,757 A | 4/1987 | Cook |
| 5,105,085 A | 4/1992 | McGuire et al. |
| 5,130,242 A | 7/1992 | Barclay |
| 5,180,499 A | 1/1993 | Hinson et al. |
| 5,244,921 A | 9/1993 | Kyle et al. |
| 5,275,732 A | 1/1994 | Wang et al. |
| 5,338,673 A | 8/1994 | Thepenier et al. |
| 5,478,208 A | 12/1995 | Kasai et al. |
| 5,527,456 A | 6/1996 | Jensen |
| 5,539,133 A | 7/1996 | Kohn et al. |
| 5,567,732 A | 10/1996 | Kyle et al. |
| 5,658,767 A | 8/1997 | Kyle |
| 5,661,017 A | 8/1997 | Dunahay et al. |
| 5,668,298 A | 9/1997 | Waldron |
| 5,776,349 A | 7/1998 | Guelcher et al. |
| 6,117,313 A | 9/2000 | Goldman et al. |
| 6,143,562 A | 11/2000 | Trulson et al. |
| 6,166,231 A | 12/2000 | Hoeksema |
| 6,372,460 B1 | 4/2002 | Gladue et al. |
| 6,524,486 B2 | 2/2003 | Borodyanski et al. |
| 6,579,714 B1 | 6/2003 | Hirabayashi et al. |
| 6,736,572 B2 | 5/2004 | Geraghty |
| 6,750,048 B2 * | 6/2004 | Ruecker et al. ............... 435/134 |
| 6,768,015 B1 | 7/2004 | Luxem et al. |
| 6,831,040 B1 | 12/2004 | Unkefer et al. |
| 7,381,326 B2 | 6/2008 | Haddas |
| 7,582,784 B2 | 9/2009 | Banavali et al. |
| 7,767,837 B2 | 8/2010 | Elliott |
| 7,868,195 B2 | 1/2011 | Fleischer et al. |
| 7,883,882 B2 | 2/2011 | Franklin et al. |
| 8,088,614 B2 | 1/2012 | Vick et al. |
| 8,404,473 B2 | 3/2013 | Kilian et al. |
| 8,569,530 B2 | 10/2013 | Hippler et al. |
| 2003/0199490 A1 | 10/2003 | Antoni-Zimmermann et al. |
| 2004/0121447 A1 | 6/2004 | Fournier |
| 2004/0161364 A1 | 8/2004 | Carlson |
| 2004/0262219 A1 | 12/2004 | Jensen |
| 2005/0048474 A1 | 3/2005 | Amburgey |
| 2005/0064577 A1 | 3/2005 | Berzin |
| 2005/0164192 A1 | 7/2005 | Graham et al. |
| 2005/0170479 A1 | 8/2005 | Weaver et al. |
| 2005/0260553 A1 | 11/2005 | Berzin |
| 2005/0273885 A1 | 12/2005 | Singh et al. |
| 2006/0045750 A1 | 3/2006 | Stiles |
| 2006/0101535 A1 | 5/2006 | Forster et al. |

(Continued)

FOREIGN PATENT DOCUMENTS

| | | |
|---|---|---|
| IN | 35/2013 A1 | 8/2013 |
| JP | 09-024362 A | 1/1997 |

(Continued)

OTHER PUBLICATIONS

Hedenskog, G., et al., Investigatin of some Methods for Increasing the Digestibility in Vitro of Microalgae, 1969, Biotechnology and Bioengineering, vol. XI, pp. 37-51.*

(Continued)

*Primary Examiner* — Yate K Cutliff
(74) *Attorney, Agent, or Firm* — Carr & Ferrell LLP

(57) ABSTRACT

Presented herein are exemplary systems and methods for extracting lipids from a wet algal biomass. An exemplary method comprises lysing a wet algal biomass with an insoluble granular lysing agent to create a lysate, creating a lipid-rich phase in the lysate, and separating the lipid-rich phase from the lysate. An exemplary system comprises a lysing station for creating a lysate from a wet algal biomass and a separation station for creating and separating a lipid-rich phase from the lysate. According to further exemplary systems and methods, ultrasound may be used in place of or in addition to a lysing agent to lyse the wet algal biomass.

8 Claims, 2 Drawing Sheets

(56) References Cited

U.S. PATENT DOCUMENTS

| | | |
|---|---|---|
| 2006/0122410 A1 | 6/2006 | Fichtali et al. |
| 2006/0166343 A1 | 7/2006 | Hankamer et al. |
| 2007/0102371 A1 | 5/2007 | Bhalchandra et al. |
| 2008/0118964 A1 | 5/2008 | Huntley et al. |
| 2008/0120749 A1 | 5/2008 | Melis et al. |
| 2008/0155888 A1 | 7/2008 | Vick et al. |
| 2008/0160591 A1 | 7/2008 | Willson et al. |
| 2008/0160593 A1 | 7/2008 | Oyler |
| 2008/0194029 A1 | 8/2008 | Hegemann et al. |
| 2008/0268302 A1 | 10/2008 | McCall |
| 2008/0275260 A1 | 11/2008 | Elliott |
| 2008/0293132 A1 | 11/2008 | Goldman et al. |
| 2009/0011492 A1 | 1/2009 | Berzin |
| 2009/0029445 A1 | 1/2009 | Eckelberry et al. |
| 2009/0081748 A1 | 3/2009 | Oyler |
| 2009/0148931 A1 | 6/2009 | Wilkerson et al. |
| 2009/0151241 A1 | 6/2009 | Dressler et al. |
| 2009/0162919 A1 | 6/2009 | Radaelli et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0325270 A1 | 12/2009 | Vick et al. |
| 2010/0022393 A1 | 1/2010 | Vick |
| 2010/0068772 A1 | 3/2010 | Downey |
| 2010/0151540 A1 | 6/2010 | Gordon et al. |
| 2010/0183744 A1 | 7/2010 | Weissman et al. |
| 2010/0196995 A1 | 8/2010 | Weissman et al. |
| 2010/0210003 A1 | 8/2010 | King et al. |
| 2010/0210832 A1 | 8/2010 | Kilian et al. |
| 2010/0260618 A1 | 10/2010 | Parsheh et al. |
| 2010/0261922 A1 | 10/2010 | Fleischer et al. |
| 2010/0314324 A1 | 12/2010 | Rice et al. |
| 2010/0327077 A1 | 12/2010 | Parsheh et al. |
| 2010/0330643 A1 | 12/2010 | Kilian et al. |
| 2010/0330658 A1 | 12/2010 | Fleischer et al. |
| 2011/0041386 A1 | 2/2011 | Fleischer et al. |
| 2011/0070639 A1 | 3/2011 | Pandit et al. |
| 2011/0072713 A1 | 3/2011 | Fleischer et al. |
| 2011/0136212 A1 | 6/2011 | Parsheh et al. |
| 2011/0196163 A1 | 8/2011 | Fleischer et al. |
| 2011/0197306 A1 | 8/2011 | Bailey et al. |
| 2011/0300568 A1 | 12/2011 | Parsheh et al. |
| 2011/0313181 A1 | 12/2011 | Thompson et al. |
| 2013/0274490 A1 | 10/2013 | Hippler et al. |

FOREIGN PATENT DOCUMENTS

| | | |
|---|---|---|
| JP | 2004300218 | 10/2004 |
| JP | 2008280252 | 11/2008 |
| WO | 2004106238 A2 | 12/2004 |
| WO | 2008060571 A2 | 5/2008 |
| WO | WO 2009/037683 A1 | 3/2009 |
| WO | 200982696 A1 | 7/2009 |
| WO | WO2011/053867 A1 | 5/2011 |

OTHER PUBLICATIONS

Santin-Montanaya, I. Optimal growth of *Dunaliella primolecta* in axenic conditions to assay herbicides, Chemosphere, 66, Elsevier 2006, pp. 1315-1322.

Felix, R. Use of the cell wall-less alga *Dunaliella bioculata* in herbicide screening tests, Annals of Applied Biology, 113, 1988, pp. 55-60.

Janssen, M. Photosynthetic efficiency of *Dunaliella tertiolecta* under short light/dark cycles, Enzyme and Microbial Technology, 29, 2001, pp. 298-305.

Saenz, M.E. Effects of Technical Grade and a Commercial Formulation of Glyphosate on Algal Population Growth, Bulletin of Environmental Contamination Toxicology, 1997, pp. 638-644.

Janseen et al., "Enclosed outdoor photobioreactors: light regime, photosynthetic efficiency,. scale-up, and future prospects," Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002/bit.10468/pdf.

Strzepek et al., "Photosynthetic architecture differs in coastal and oceanic diatoms," Nature vol. 431, p. 689-692, Oct. 7, 2004. Entire document, especially: abstract, p. 689, col. 2; p. 691, Table 1 [online] Retrieved from the Internet on [Oct. 5, 2010]. Retrieved from: <URL: http://www.nature.com/nature/journal/v431/n7009/pdf/nature09254.pdf.

Zitelli et al., "Mass cultivation of *Nannochloropsis* sp. in annular reactors," Journal of Applied Phycology vol. 15, p. 107-113, Mar. 2003, Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext.pdf.

Csogor et al., "Light distribution in a novel photobioreactor—modeling for optimization," Journal of Applied Phycology, vol. 13, p. 325-333, May 2001, Entire document, especially: Fig 2, p. 327; Table 1, p. 327; Fig 7, p. 330 [online]. Retrieved from the Internet on [Oct. 5, 2010]. Retrieved from: <URL: http://www.springerlink.com/content/p77j66g3j2133522/fulltext.pdf.

Kureshy, et al. "Effect of Ozone Treatment on Cultures of *Nannochloropsis oculata, Isochrysis galbana*, and *Chaetoceros gracilis*." Journal of the World Aquaculture Society, Dec. 1999, vol. 30, No. 4, pp. 437-480; p. 473, Abstract; p. 475, "*Nannochloropsis oculata*" Section; p. 476, Table 1; p. 476, Table 2; p. 479, left column, para 2. NCBI entry EE109892 (Jul. 27, 2006) [Retrieved from the Internet on Oct. 19, 2009; <http://www.ncbi/nlm.nih.gov/nucest/EE109892?ordinalpos=1&itool=EntrezSystem2.PEntrez.Sequence.Sequence_ResultsPanel.Sequence_RVDocSum>].

Knuckey et al., "Production of Microalgal Concentrates by Flocculation and Their Assessment as Aquaculture Feeds," Acquacultural Engineering 35 (2006) 300-313.

Grima et al., "Recovery of Microalgal Biomass in Metabolites: Process Options and Economics," Biotechnology Advances 20 (2003) 491-515.

Lee et al. Isolation and Characterization of a Xanthophyll Aberrant Mutant of the Green Alga *Nannochloropsis oculata* Marine Biotechnology vol. 8, 238-245 (2006) (p. 239 col. 1 para 1; p. 239 col. 2 para 4; p. 240 col. 1 para 2; p. 242 col. 2 para 2; p. 241 Table 1, Fig 2; p. 242 Table 2).

Berberoglu et al. Radiation characteristics of *Chlamydomonas reinhardtii* CC125 and itstruncated chlorophyll antenna transformants tla1, tlaX and tla1-CW+. International Journal of Hydrogen Energy.2008 vol. 33 pp. 6467-6483, especially the abstract.

Ghirardi et al. Photochemical apparatus organization in the thylakoid membrane of *Hordeum vulgare* wild type and chlorophyll b-less chlorine f2 mutant. Biochimica et Biophysica Acta (BBA)—Bioenergetics. vol. 851, Issue 3, Oct. 8, 1986, pp. 331-339 (abstract only).

Steinitz et al. A mutant of the cyanobacterium *Plectonema boryanum* resistant to photooxidation. Plant Science Letters. vol. 16, Issues 2-3, Oct. 1979, pp. 327-335 (abstract only).

Koller et al. Light Intensity During Leaf Growth Affects Chlorophyll Concentration and CO2 Assimilation of a Soybean Chlorophyll Mutant. Crop Sci. 1974. vol. 14 pp. 779-782 (abstract only).

Shikanai et al. Identification and Characterization of *Arabidopsis* Mutants with Reduced Quenching of Chlorophyll Fluorescence. Plant and Cell Physiology, 1999, vol. 40, No. 11. pp. 1134-1142 (abstract only).

Loury, Maurice Chem. Abstr., Method for rapid conversion of fats to methyl esters, Revue Francaise des Corps Gras (1967), 14 (6), 383-9. (NPL 0009).

Cravotto et al., Improved extraction of vegetable oils under high-intensity ultrasound and/or microwaves, Ultrasonics Sonochemistry 15:898-9002 (2008). (NPL 0011).

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601. (NPL 0015).

Hallmann et al., "Genetic Engineering of the Multicellular Green Alga Volvox: A Modified and Multiplied Bacterial Antibiotic Resis-

(56) References Cited

OTHER PUBLICATIONS tance Gene as a Dominant Selectable Marker" The Plant Journal 17(1): 99-109 (Jan. 1999). (NPL 0020).

Kindle et al. "Stable Nuclear Transformation of *Chlamydomonas* Using the *Chlamydomonas* Gene for Nitrate Reductase" The Journal of Cell Biology 109 (6, part 1): 2589-2601. (NPL 0024).

Prein et al. "A Novel Strategy for Constructing N-Terminal Chromosomal Fusions to Green Fluorescent Protein in the Yeast *Saccharomyces cerevisiae*" FEBS Letters 485 (2000) 29-34 (NPL 0034).

Schiedlmeier et al., "Nuclear Transformation of *Volvox carteri*" Proceedings of the National Academy of Sciences USA 91(11): 5080-5084 (May 1994). (NPL 0039).

Wendland et al. "PCR-Based Methods Facilitate Targeted Gene Manipulations and Cloning Procedures" Curr.Gen. (2003) 44:115-123 (NPL 0046).

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Molnar et al., "Highly Specific Gene Silencing by Artificial MicroRNAs in the Unicellular Agla Chlamydomonas reinhardtii," Plant Jour. ePub Jan. 17, 2009, vol. 58, No. 1, pp. 157-164 (Abstract Only).

Chen et al., "Conditional Production of a Functional Fish Growth Hormone in the Transgenic Line of Nannochloropsis oculata (Eustigmatophyceae)," J. Phycol. Jun. 2008, vol. 44, No. 3, pp. 768-776.

Nelson et al., "Targeted Disruption of NIT8 Gene in Chlamydomonas reinhardtii." Mol. Cell. Bio. Oct. 1995, vol. 15, No. 10, pp. 5762-5769.

Ben-Amotz, Ami. "Large-Scale Open Algae Ponds," presented at the NREL-AFOSR Joint Workshop on Algal Oil for Get Fuel Production in Feb. 2008.

Ebeling et al., "Design and Operation of a Zero-Exchange Mixed-Cell Raceway Production System," 2nd Int'l Sustainable Marine Fish Culture Conference and Workshop, Oct. 2005.

Ebeling et al., "Mixed-Cell Raceway: Engineering Design Criteria, Construction, and Hydraulic Characterization," North American Journal of Aquaculture, 2005, 67: 193-201 (abstract only).

Labatut et al., "Hydrodynamics of a Large-Scale Mixed-Cell Raceway (MCR): Experimental Studies," Aquacultural Engineering vol. 37, Issue 2, Sep. 2007, pp. 132-143.

Kizilisoley et al., "Micro-Algae Growth Technology Systems," Presented by Selim Helacioglu, Soley Institute, 2008.

Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.

Carvalheiro et al., "Hemicellulose Biorefineries: A Review on Biomass Pretreatments," Journal of Scientific & Industrial Research, vol. 67, Nov. 2008, pp. 849-864.

Lotero et al., "Synthesis of Biodiesel via Acid Catalysis," Ind. Eng. Chem. Res., 2005, pp. 5353-5363.

Gouveia et al., "Microalgae as a raw material for biofuels production," J. Ind. Microbiol. Biotechnol, 2009, vol. 36, 269-274.

International Search Report and Written Opinion of the International Searching Authority mailed Jan. 6, 2011 for Application No. PCT/US2010/054861, filed Oct. 29, 2010.

Chen et al., "Subcritical co-solvents extraction of lipid from wet microalgae pastes of Nannochloropsis sp.," Eur. J. . Lipid Sci. Technol., vol. 114, 2012, pp. 205-212.

Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.

Pitipanapong et al., "New approach for extraction of charantin from Momordica charantia with pressurized liquid extraction," Separation and Purification Technology, vol. 52, Issue 3, Jan. 2007.

International Search Report and Written Opinion of the International Searching Authority mailed Feb. 5, 2009 for Application No. PCT/US2008/087722, filed Dec. 19, 2008.

Examination Report mailed Aug. 15, 2013 in Australian Application No. 2010313246 filed Oct. 29, 2010.

Second Examination Report mailed Dec. 17, 2013 in Australian Application No. 2010313246 filed Oct. 29, 2010.

Lubian, L. M., "Concentrating Cultured Marine Microalgae with Chitosan." Aquaculture Engineering, 8, 257-265 (1989).

Divakaran, R. & Sivasankara Pillai, VN, "Flocculation of Algae Using Chitosan." Journal of Applied Phycology, 14, 419-422 (2002).

Farid, M. S., Shariati, A., Badakhshan, A., & Anvaripour, B., "Using Nano-Chitosan for Harvesting Microalga Nannochloropsis sp." Bioresource Technology, 131, 555-559 (2013).

\* cited by examiner

SYSTEMS AND METHODS FOR EXTRACTING LIPIDS FROM WET ALGAL BIOMASS

BACKGROUND OF THE INVENTION

1. Field of the Invention

This invention relates to extracting lipids from algal biomass, and more particularly to low energy techniques using an insoluble granular lysing agent or ultrasound to extract lipids from wet algal biomass.

2. Description of Related Art

Microalgae differentiate themselves from other single-cell microorganisms in their natural ability to accumulate large amounts of lipids. Because most lipidic compounds have the potential to generate biofuels and renewable energy, there is a need for efficient systems and methods for extracting lipids from wet algal biomass.

SUMMARY OF THE INVENTION

Presented herein are exemplary systems and methods for extracting lipids from a wet algal biomass. An exemplary method comprises lysing a wet algal biomass with an insoluble granular lysing agent to create a lysate, creating a lipid-rich phase in the lysate, and separating the lipid-rich phase from the lysate.

Exemplary methods include using an insoluble granular lysing agent having a grain size dispersion of 10 to 1000 micrometers. In some embodiments, the insoluble granular lysing agent may be sand. In other embodiments, the insoluble granular lysing agent may be chalk, gypsum, or fly ash, for example. In various embodiments, the wet algal biomass is in the presence of an extraction solvent. The extraction solvent may be monophasic and multipolar.

An exemplary system comprises a lysing station for creating a lysate from a wet algal biomass and a separation station for creating and separating a lipid-rich phase from the lysate.

According to further exemplary systems and methods, ultrasound may be used in place of or in addition to a lysing agent to lyse the wet algal biomass.

DETAILED DESCRIPTION

Microalgae produce large amounts of lipids. Lipids may be extracted from algal biomass by the use of solvents. For instance, hexane may be used to extract lipids and carotenoids from algal biomass. Acetone and carbon dioxide are other solvents that may be used to extract lipids and carotenoids from algal biomass.

Solvent extraction, however, is generally only effective if the lipid-rich biomass has a low moisture level (below approximately 12%, as measured by the content of water in the total wet algal biomass). Lipids, especially polar lipids, are partially soluble in water, which reduces the hexane extraction efficiency on wet algal biomass. Further, crushing or grinding algal cells in order to expose the intracellular biomass is generally only effective on dry algal biomass. Additionally, dewatering algal biomass by filtration is generally not very effective. Membranes, air flotation, and press, belt or drum filtration typically yield a maximum solid content of 30% (or conversely a moisture content of 70% or above). Reducing this moisture level further may be achieved by drying, which is a complicated and expensive operation that makes the production of lipids and carotenoids from algae very energy inefficient and expensive. The exemplary systems and methods described herein increase the efficiency and decrease the cost of lipid extraction from wet algal biomass.

Figure 1:
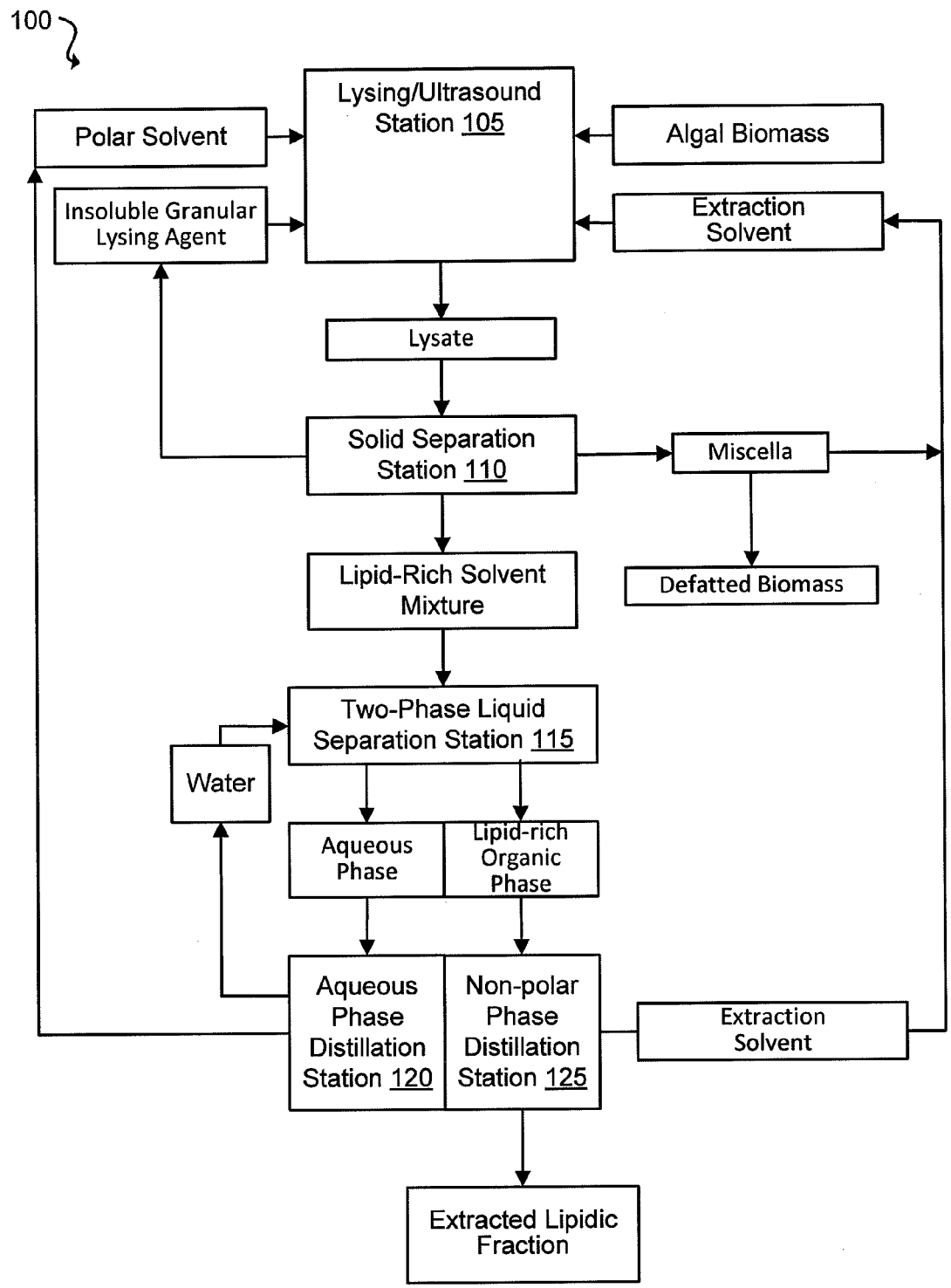
FIG. 1 shows an exemplary system for extracting lipids from wet algal biomass according to one embodiment.

FIG. 1 shows an exemplary system for extracting lipids from wet algal biomass according to one embodiment. The exemplary system 100 comprises a lysing/ultrasound station 105, a solid separation station 110, a two-phase liquid separation station 115, a polar aqueous phase distillation station 120, a non-polar organic phase distillation station 125, and a lipid station (not shown).

According to one embodiment, the lysing/ultrasound station 105 receives centrifuged algal biomass, polar and non-polar solvents, and a lysing agent. This mixture may be mixed, vortexed, or otherwise agitated to induce cell lysis. According to a further embodiment, cell lysing and solvent mixing take place simultaneously and continuously in a stirred tank. Agitation in the tank may be provided in different ways, including using shaking containers. The tank provides an environment where the solvents may come into effective contact with the lysed algal biomass. In an alternative embodiment, jet mixing or ultrasound may be used to agitate the lysing agent/biomass mixture.

According to an alternative embodiment, ultrasound may be used in place of the lysing agent. For example, the use of ultrasonic cell disruptor probes may be an effective cell lysis technique. A similar technique includes using a continuous flow-through ultrasonication chamber for lysing cells in an algae slurry.

In various embodiments, the solid separation station 110 receives the mixture of polar and non-polar solvents, lysing agent and lysed algal biomass. At the solid separation station 110, via centrifugation, the lysing agent, lipid-rich solvent mixture, and miscella are each isolated and directed to a different destination. The lipid-rich solvent mixture is sent to the two-phase liquid separation station 115, and the miscella is sent to a solvent recovery station (not shown). The miscella is subject to flash evaporation or similar operation to evaporate the solvents, which are subsequently condensed and recycled to the process.

The two-phase liquid separation station 115, according to one embodiment, pools the lipid-rich solvent mixture received from the solid separation station 110. The lipid-rich solvent mixture is mixed with water at the two-phase liquid separation station 115. The resulting mixture is centrifuged into two portions: an aqueous phase that includes polar solvent, and an organic phase (lipidic fraction) that includes non-polar solvent. The aqueous phase is sent to the polar aqueous phase distillation station 120 and the organic phase is sent to the non-polar organic phase distillation station 125.

At the polar aqueous phase distillation station 120, in various embodiments, the aqueous phase is distilled to recover the polar solvent. At the non-polar organic phase distillation station 125, the organic phase is distilled to recover two portions: the lipidic portion and the non-polar solvent portion. The lipidic portion is sent to the lipid station (not shown). At the lipid station, according one exemplary embodiment, the lipidic portion is heated to evaporate some or all of the remaining solvents within the lipidic portion.

Figure 2:
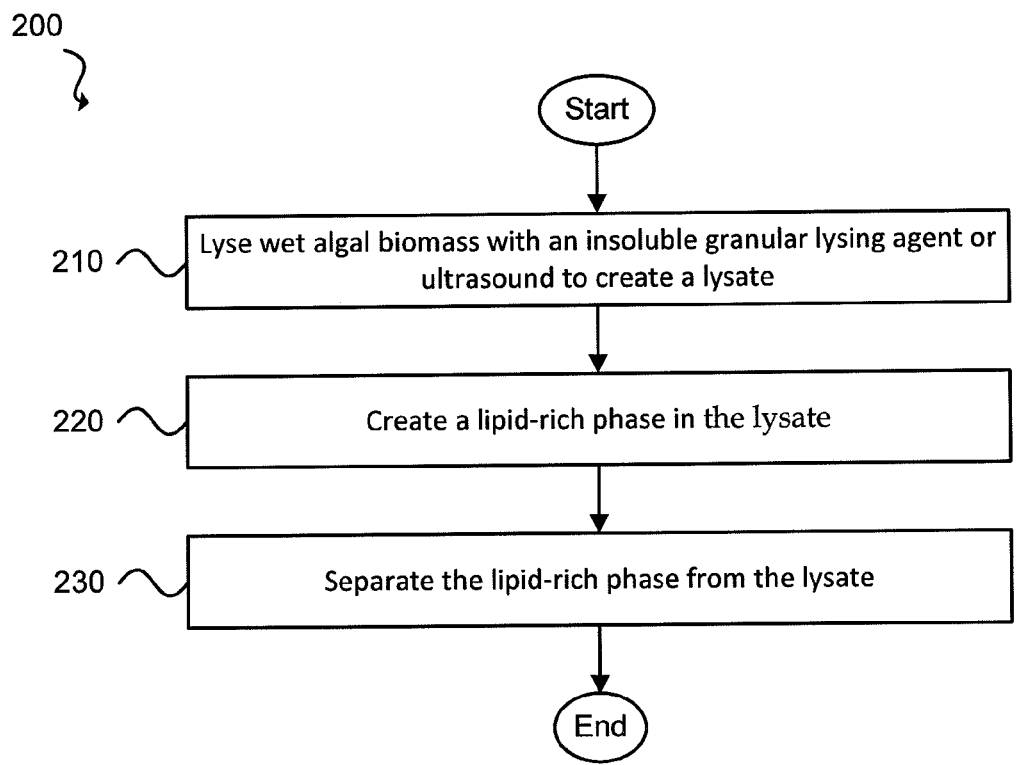
FIG. 2 is a diagram showing an exemplary method for extracting lipids from wet algal biomass.

FIG. 2 is a diagram showing an exemplary method 200 for extracting lipids from wet algal biomass.

As a preliminary step, wet algal biomass is centrifuged to increase its solid content to a range of approximately fifteen percent (15%) to thirty percent (30%). According to another exemplary embodiment, membrane filtration is used instead of centrifugation.

At step 210, wet algal biomass is lysed with an insoluble granular lysing agent and/or ultrasound to create a lysate. In various embodiments, the lysing agent is an insoluble granular lysing agent with a grain size dispersion of 10 to 1000 micrometers. The insoluble granular lysing agent may be sand, chalk, gypsum or fly ash. The amount of insoluble granular lysing agent used may be a quantity effective to make the intra-cellular biomass available for contact with the polar and non-polar solvents. The amount of insoluble granular lysing agent may be equivalent to the dry weight of the wet algal biomass.

According to an alternative embodiment, ultrasound may be used in place of the lysing agent. For example, the use of ultrasonic cell disrupter probes may be an effective cell lysis technique. A similar technique includes using a continuous flow-through ultrasonication chamber for lysing cells in an algae slurry.

Additionally, polar and non-polar solvents may be added to the algal biomass-lysing agent mixture to create a slurry. In one exemplary embodiment, the slurry may have a water content ranging between 10% and 90% by weight. The polar solvent may be a ketone, such as acetone, methyl-ethyl ketone or di-ethyl ketone; or an alcohol, such as methanol, ethanol, propanol, butanol, isopropanol; or an alkyl halide such as di-chloro-methane and tri-chloro-ethane; or a furane such as tetra-hydro-furane. The polar solvent, according to another exemplary embodiment, may also be dimethyl ether. In various exemplary embodiments, the non-polar solvents may include hydrocarbons such as propane, butane, pentane, hexane; ethers such as diethyl ether, diisopropyl ether, methyl tert-butyl ether; esters such as ethyl propanoate; or halocarbons such as trichloroethylene etc. Typically, the amount of polar and non-polar solvents required is proportional to the amount of water present in the biomass. In various embodiments, the mixture of polar and non-polar solvents is added in the desired solvent-extractible volume ratio. For instance, 20 to 100 volumes of solvents are usually required to extract one volume of lipids and carotenoids from algal biomass. Then, the mixture of polar and non-polar solvents, lysing agent and algal biomass is vortexed to induce cell lysis. The resulting solids are centrifuged from the vortexed mixture of polar and non-polar solvents, lysing agent and algal biomass. According to one embodiment, the lysing agent, lipid-rich solvent mixture, and miscella are each isolated.

At step 220, a lipid-rich phase is created in the lysate. According to various exemplary embodiments, the pooled lipidic fraction (less the lysing agent) is mixed with water.

At step 230, the lipid-rich phase is separated from the lysate. In one exemplary embodiment, the mixture of the lipidic fraction and water is centrifuged into two portions: an aqueous phase that includes polar solvent and an organic phase (lipidic fraction) that includes non-polar solvent. A liquid-liquid separator may be used to generate the two phases. The aqueous phase is distilled to recover the polar solvent. The organic phase is distilled to recover two portions: the lipidic portion and the non-polar solvent portion. Then the lipidic portion is heated to evaporate some or all of the remaining solvents within the lipidic portion.

EXAMPLE ONE

Fifty milliliters (50 mls) of harvested microalgae liquid culture of a density of about 300 milligrams per liter of ash-free dry biomass is centrifuged in 50 ml conical tubes at 2000 RCF for 15 minutes. The supernatant is discarded and the pellet is covered with a portion of sand, chalk, gypsum or fly ash with a volume approximately equal to that of the cell pellet. 5 ml of solvent mixture is added. The solvent may be methanol: chloroform 2:1, acetone: hexane 2:1, or any similar single phase mixture of solvents of differing polarity that form a single phase when mixed with the wet biomass and are capable of dissolving lipids.

The tube is then vortexed for five minutes to lyse the cells, and centrifuged again for 15 minutes at 2000 RCF. The supernatant is collected and fresh solvent is added to the pellet. The tube is again vortexed and centrifuged. The supernatant is collected and the pellet vortexed again with fresh solvent. After centrifugation a fourth extraction/centrifugation is performed and the 4 supernatants are combined. The lysing agent and the defatted biomass form separate layers in the centrifuge tube which may be separated by scooping the defatted biomass off the top.

The combined supernatants are centrifuged to remove any residual suspended solids. The supernatant is then mixed with 10 mls of water and the mixture is centrifuged for 5 minutes to yield a biphasic system with a dark, pigment rich non-polar solvent layer and a clear water/polar solvent layer. The layers are separated and the non-polar layer is evaporated to dryness under a stream of nitrogen to yield the microalgal lipids.

EXAMPLE TWO 50 mls of harvested microalgae liquid culture of a density between 200 and 3000 milligrams per liter of ash-free dry biomass is centrifuged in 50 ml conical tubes at 2000 RCF for 15 minutes. The supernatant is discarded and the pellet is exposed to a 20 kHz ultrasonic pulse for 3 minutes from a Branson 450 Sonifier. 5 ml of solvent mixture is added. The solvent may be methanol:chloroform 2:1, acetone hexane 2:1, or any similar single phase mixture of solvents of differing polarity that form a single phase when mixed with the wet biomass and are capable of dissolving lipids. The tube is then vortexed for 5 minutes to mix the lysed cells with the solvent, and centrifuged again for 15 minutes at 2000 RCF. The supernatant is collected and fresh solvent is added to the pellet. The tube is again vortexed and centrifuged. The supernatant is collected and the pellet vortexed again with fresh solvent. After centrifugation a fourth extraction/centrifugation is performed and the 4 supernatants are combined. The combined supernatants are centrifuged to remove any residual suspended solids. The supernatant is then mixed with 10 mls of water and the mixture is centrifuged for 5 minutes to yield a biphasic system with a dark, pigment rich non-polar solvent layer and a clear water/polar solvent layer. The layers are separated and the non-polar layer is evaporated to dryness under a stream of nitrogen to yield the microalgal oils.

While various embodiments have been described herein, it should be understood that they have been presented by way of example only, and not limitation. Thus, the breadth and scope of a preferred embodiment should not be limited by any of the herein-described exemplary embodiments.

The invention claimed is:

1. A method comprising:
   lysing a wet algal biomass with an insoluble granular lysing agent to create a lysate;
   creating a lipid-rich phase in the lysate; and
   separating the lipid-rich phase from the lysate.

2. The method of claim 1, wherein the insoluble granular lysing agent has a grain size dispersion of 10 to 1000 micrometers.

3. The method of claim 1, wherein the insoluble granular lysing agent is sand.

4. The method of claim 1, wherein the insoluble granular lysing agent is chalk.

5. The method of claim 1, wherein the insoluble granular lysing agent is gypsum.

6. The method of claim 1, wherein the insoluble granular lysing agent is fly ash.

7. The method of claim 1, wherein the wet algal biomass is in the presence of an extraction solvent.

8. The method of claim 7, wherein the extraction solvent is monophasic and multipolar.

* * * * *